United States Patent

Seeger et al().

[11] 4,021,479
[45] May 3, 1977

[54] DERIVATIVES OF 4-(4-BIPHENYLYL)-BUTYRIC ACID

[75] Inventors: Ernst Seeger; Wolfhard Engel; Josef Nickl; Helmut Teufel, all of Biberach an der Riss, Germany

[73] Assignee: Boehringer Ingelheim GmbH, Ingelheim am Rhein, Germany

[22] Filed: Oct. 15, 1973

[21] Appl. No.: 406,196

Related U.S. Application Data

[63] Continuation-in-part of Ser. No. 234,346, March 13, 1972, abandoned.

[30] Foreign Application Priority Data

Mar. 17, 1971 Germany .......................... 2112716
Mar. 17, 1971 Germany .......................... 2112715
Mar. 17, 1971 Germany .......................... 2112840

[52] U.S. Cl. .................. 260/520 B; 260/343.6; 260/465 D; 260/469; 260/471 R; 260/473 A; 260/501.1; 260/501.11; 260/501.16; 260/501.17; 260/515 R; 260/515 A; 260/518 R; 260/518 A; 260/519; 424/279; 424/304; 424/308; 424/309; 424/316; 424/317; 424/319

[51] Int. Cl.$^2$ ................ C07C 63/333; C07C 65/14

[58] Field of Search .......... 260/515 R, 520 B, 469, 260/343.6, 473 A, 465 D, 471 R

[56] References Cited

UNITED STATES PATENTS 3,462,483   8/1969   Petrow et al. .................... 260/520
3,867,434   2/1975   Diamond ...................... 260/515 A Primary Examiner—Jane S. Myers Attorney, Agent, or Firm—Hammond & Littell

[57] ABSTRACT

Compounds of the formulas

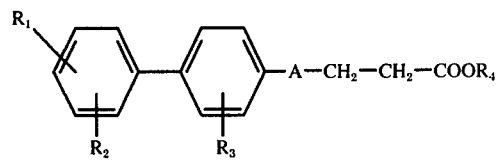

and

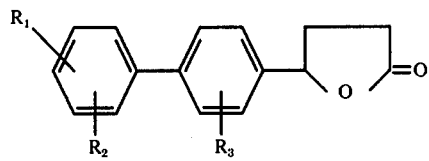

wherein
A is —$CH_2$— or —CH(OH)—,
$R_1$ is hydrogen, halogen or, when $R_2$ and $R_3$ are other than both hydrogen, also methyl,
$R_2$ is hydrogen, halogen, cyano, nitro, amino or (alkanoyl of 1 to 4 carbon atoms)-amino,
$R_3$ is hydrogen or halogen,
provided, however, that at least one of $R_1$, $R_2$ and $R_3$ is other than hydrogen, and
$R_4$ is hydrogen or alkyl of 1 to 4 carbon atoms, and non-toxic salts of the free acids ($R_4$ = H) formed with inorganic or organic bases; the compounds as well as their salts are useful as antiphlogistics and antiproliferatives.

1 Claim, No Drawings

DERIVATIVES OF 4-(4-BIPHENYLYL)-BUTYRIC ACID

This is a continuation-in-part of copending application Ser. No. 234,346, filed Mar. 13, 1972, now abandoned.

This invention relates to a novel class of compounds represented by the formulas

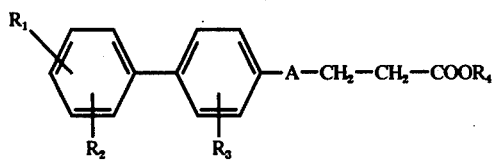

and

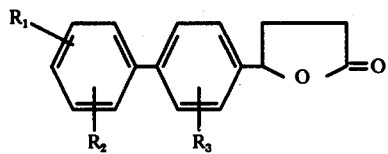

wherein

A is —$CH_2$— or —CH(OH)—, $R_1$ is hydrogen, halogen or, when $R_2$ and $R_3$ are other than both hydrogen, also methyl, $R_2$ is hydrogen, halogen, cyano, nitro, amino or (alkanoyl of 1 to 4 carbon atoms)-amino, $R_3$ is hydrogen or halogen, provided, however, that at least one of $R_1$, $R_2$ and $R_3$ is other than hydrogen, and $R_4$ is hydrogen or alkyl of 1 to 4 carbon atoms, and non-toxic salts of the free acids ($R_4$ = H) formed with inorganic or organic bases.

The compounds of the instant invention may be prepared by a number of different methods, among which the following are most convenient and efficient.

METHOD A

For the preparation of a compound of the formula I wherein A is —$CH_2$—, by reducing a compound of the formula

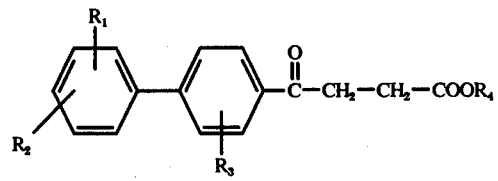

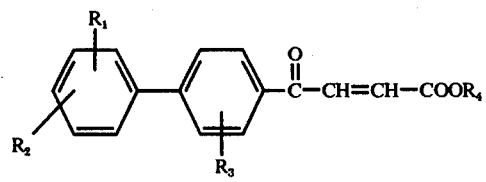

or

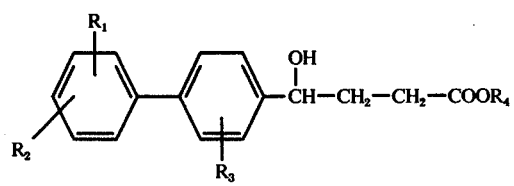

wherein $R_1$, $R_2$, $R_3$ and $R_4$ have the same meanings as in formula I.

The reduction is preferably effected by means of catalytically activated hydrogen in a polar solvent medium, such as glacial acetic acid, in the presence of a strong acid, such as perchloric acid or orthophosphoric acid, at a temperature between 0° and 50° C but preferably at room temperature, and at a hydrogen pressure of 1 to 5 atmospheres, although higher hydrogen pressures may be employed as well. Palladium/barium sulfate or palladium/animal charcoal have proved to be particularly suitable as catalysts for this reduction. In those instances where $R_2$ in formulas II to IV is nitro, this substituent is simultaneously reduced to amino by the catalytic hydrogenation.

The reduction may also be effected with nascent hydrogen, particularly by the method of Clemmensen, that is, with amalgamated zinc in the presence of aqueous hydrochloric acid, such as concentrated hydrochloric acid, and of an inert solvent, such as toluene or tetrahydrofuran, at a temperature up to the boiling point of the solvent. In those instances where $R_2$ in formulas II to IV is nitro, this substituent is simultaneously reduced to amino by the nascent hydrogenation.

4-(4-biphenylyl)-4-oxo-butyric acid compounds of the formula II may also be reduced by the method of Wolff-Kishner, and especially by the variation thereof discovered by Huang-Minlon, namely by heating a compound of the formula II with hydrazine hydrate in the presence of a suitable inert solvent, such as diethyleneglycol and of an alkali metal hydroxide, such as sodium hydroxide, to a temperature between 70° and 250° C. The reaction product, i.e. the alkali metal salt of the corresponding acid of the formula I wherein A is —$CH_2$—, may be readily isolated from the reaction mixture or, upon acidifying the reaction mixture, the corresponding free acid.

Finally, the compounds of the formulas II to IV may also be reduced with hydroiodic acid. The reduction is effected by heating the starting compound in a polar solvent, such as glacial acetic acid, in the presence of hydrogen iodide, and optionally in the presence of red phosphorus, at elevated temperatures, preferably at the boiling point of the particular solvent. After completion of the reduction reaction, the free iodine which may have separated out is removed with sodium thiosulfate, for example.

The starting compounds of the formula II may be prepared by methods A, B, C or D described in said copending application Ser. No. 234,346, now abandoned.

The 4-(4-biphenylyl)-4-oxo-crotonic acid compounds of the formula III may, for example, be prepared by reacting a correspondingly substituted biphenylyl methyl ketone with glyoxylic acid hydrate in the presence of an acid condensation agent, preferably formic acid or acetic acid. In this manner the following starting compounds of the formula III were obtained:

4-(2'-Fluoro-4-biphenylyl)-4-oxo-crotonic acid, m.p. 167° C;

4-(4'-Fluoro-4-biphenylyl)-4-oxo-crotonic acid, m.p. 191°–193° C; and 4-(2-Chloro-4-biphenylyl)-4-oxo-crotonic acid, m.p. 162.5°–164.5° C.

The 4-(4-biphenylyl)-4-hydroxy-butyric acid compounds of the formula IV may be prepared, for example, by reducing a compound of the formula II with a primary or secondary alcohol in the presence of an alcoholate, such as with isopropanol and aluminum isopropylate, at elevated temperatures, preferably at the boiling point of the solvent medium, while continuously distilling the ketone released by the reaction, such as acetone, out of the reaction mixture. In this manner the following compounds were prepared:

Sodium 4-(2'-chloro-4-biphenylyl)-4-hydroxy-butyrate, double m.p. 90°–95° C and 130°–133° C (ethanol);
Cyclohexylamine 4-(2',4'-dichloro-4-biphenylyl)-4-hydroxy-butyrate, m.p. 157°–159° C (water); and
Cyclohexylamine 4-(4'-fluoro-4-biphenylyl)-4-hydroxy-butyrate, m.p. 175°–177° C.

METHOD B

For the preparation of a compound of the formula I wherein A is —$CH_2$—, $R_2$ is 4'-nitro and $R_3$ is hydrogen, by nitrating a 4-(4-biphenylyl)-butyric acid compound of the formula

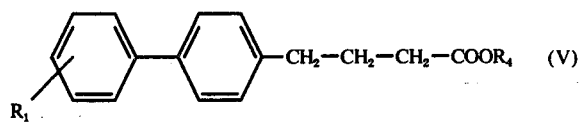

wherein $R_1$ and $R_4$ have the same meanings as in formula I.

The nitration is preferably effected with fuming nitric acid at a temperature between 0° and 50° C, preferably between 25° and 30° C, in the presence of a polar solvent medium, such as glacial acetic acid. However, mixtures of nitric acid and sulfuric acid or of nitric acid and acetic acid anhydride may also be used as the nitrating agent.

METHOD C

For the preparation of a compound of the formula I wherein A is —CH(OH)—, by reducing a 4-(4-biphenylyl)-4-oxo-butyric acid compound of the formula II.

The reduction may be effected with a complex metal hydride, such as sodium borohydride, lithium borohydride, potassium borohydride or lithium aluminum hydride. However, the reduction with lithium aluminum hydride may be applied only to a carboxylic acid of the formula II wherein $R_2$ has the meanings defined in connection with formula I except nitro or cyano, because these substituents may possibly be affected by the reduction. The reduction with lithium aluminum hydride is effected in a suitable solvent or suspension medium, such as tetrahydrofuran, at a temperature between —40° and 0° C. If the reduction is effected with an alkali metal borohydride, a salt of an acid of the formula II is preferably used as the starting compound, and the salt is reduced in solution in a suitable solvent, such as alkanols, aqueous alkanols or water, at a temperature between —15° and +100° C, preferably between 0° and 45° C.

The reduction may also be effected with a primary or secondary alcohol in the presence of an alcoholate, such as with isopropanol in the presence of aluminum isopropylate, at elevated temperatures, preferably at the boiling point of the solvent medium, while continuously distilling the ketone released by the reaction, such as acetone, out of the reaction mixture. In most instances, this reduction method yields a mixture of a 4-(4-biphenylyl)4-hydroxy-butyric acid compound of the formula I and the corresponding lactone of the formula Ia, from which the latter may readily be isolated and converted into the 4-hydroxy-acid, as described below.

The reduction may further also be effected with catalytically activated hydrogen, but it should be noted that nitro-substituents on the phenyl rings are simultaneously reduced to amino-substituents thereby. The reduction with catalytically activated hydrogen is preferably carried out with palladized barium sulfate as the catalyst, in aqueous-alkaline solution, at a hydrogen pressure of preferably 0.1 to 5 atmospheres, and at a temperature between 0° and 50° C, but preferably at room temperature. The catalytic hydrogenation may also be performed in the presence of Raney nickel or Raney cobalt as the catalyst and in an inert solvent medium, such as ethyl acetate, methanol, dioxane or tetrahydrofuran, at a temperature above 50° C.

Finally, the reduction may also be effected with nascent hydrogen, but this hydrogenation may not be applied to all the compounds embraced by formula II. Thus, only a compound of the formula II wherein $R_1$, $R_2$ and $R_3$ are other than chlorine, bromine, cyano or nitro may be reduced with nascent hydrogen generated in situ by the action of metallic sodium upon an alkanol, such as ethanol, at a temperature up to the boiling point of the particular alkanol. On the other hand, a compound of the formula II wherein $R_1$, $R_2$ and $R_3$ are other than bromine, cyano or nitro may be reduced with nascent hydrogen generated in situ by the action of magensium filings upon a lower alkanol, such as methanol, at room temperature.

The 4-(4-biphenylyl)-4-hydroxy-butyric acids and their esters of the formula I obtained in this manner readily convert into the corresponding lactones of the formula I2, especially in solution, accompanied by spontaneous dehydration; the esters change into the lactones in the presence of a small amount of an acid or a base [cf. also H. Kröper in Houben-Weyl, Methoden der organischen Chemie, VI/2, 571, Thieme Verlag, Stuttgart, Germany (1963)].

Conversely, the lactones of the formula Ia can very readily be converted into the corresponding acids of the formula I wherein A is —CH(OH)—; thus, the lactones quickly undergo cleavage upon being heated with an equivalent amount of an alkali metal hydroxide or an alkaline earth metal hydroxide to yield the corresponding alkali metal or alkaline earth metal salts of the corresponding 4-(4-biphenylyl)-4-hydroxy-butyric acid, from which the free acids may be obtained by careful acidification.

METHOD D

For the preparation of a compound of the formula I wherein $R_2$ is other than nitro and A is —CH(OH)—, by reducing a 4-(4-biphenylyl)-4-hydroxy-crotonic acid compound of the formula

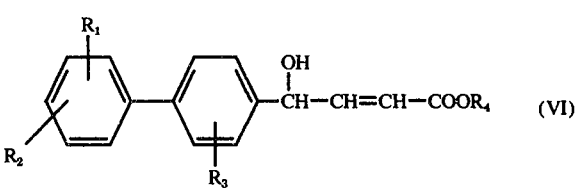

wherein $R_1$, $R_2$, $R_3$ and $R_4$ have the same meanings as in formula I, or a salt thereof formed with an inorganic or organic base.

The reduction is effected with catalytically activated hydrogen in a suitable solvent medium, such as an alcohol, water or mixtures of an alcohol and water; especially suitable alcohols are methanol, ethanol or isopropanol. Preferred catalysts are Raney nickel, Raney cobalt, platinum or palladium. The catalytic reduction is carried out at a temperature between 0° and 80° C, but preferably at room temperature, and preferably at a hydrogen pressure of 1 to 5 atmospheres.

The starting compounds of the formula VI needed for this method may be prepared by reducing a 4-(4-biphenylyl)-4-oxo-crotonic acid compound of the formula III. The reduction is effected, for example, with a primary or secondary alcohol in the presence of an alcoholate, such as with isopropanol in the presence of aluminum isopropylate, at elevated temperatures, preferably at the boiling point of the solvent medium, while continuously distilling the ketone, such as acetone, released by the reaction out of the reaction mixture. Using this method, the following starting compounds of the formula VI were prepared:

4-(2'-Fluoro-4-biphenylyl)-4-hydroxy-crotonic acid, m.p. of the sodium salt: 230°–232° C;
4-(2'-Chloro-4-biphenylyl)-4-hydroxy-crotonic acid, m.p. of the isobutylamine salt: 157°–159° C;
4-(4'-Fluoro-4-biphenylyl)-4-hydroxy-crotonic acid; m.p. 165°–166° C;
4-(4'-Chloro-4-biphenylyl)-4-hydroxy-crotonic acid, m.p. 185°–186° C;
4-(2',4'-Dichloro-4-biphenylyl)-4-hydroxy-crotonic acid, m.p. 113°–115° C;
4-(3',4'-Dichloro-4-biphenylyl)-4-hydroxy-crotonic acid, m.p. of the cyclohexylamine salt: 182°–183° C; and
4-(4'-Chloro-2'-cyano-4-biphenylyl)-4-hydroxy-crotonic acid, m.p. of the cyclohexylamine salt: 188°–189° C.

METHOD E

For the preparation of a compound of the formula I wherein $R_2$ is amino ($-NH_2$) and A is $-CH(OH)-$, by reducing a compound of the formula

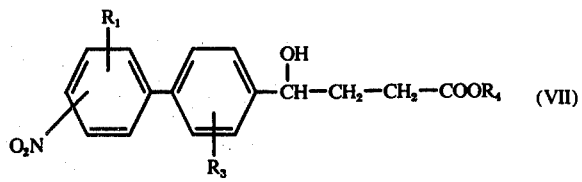

wherein $R_1$, $R_3$ and $R_4$ have the same meanings as in formula I.

The reduction is advantageously effected with catalytically activated hydrogen, for instance with hydrogen at a pressure of 5 atmospheres at room temperature in the presence of a hydrogenation catalyst, such as Raney nickel or Raney cobalt. However, the reduction may also be effected with nascent hydrogen generated by the action of a metal, such as zinc, upon an acid, such as acetic acid.

The free carboxylic acids ($R_4 = H$) of the formula I, wherein A is $-CH_2-$, obtained by the above-described methods may, if desired, be converted into the corresponding alkyl esters ($R_4 =$ alkyl) by conventional esterification procedures, and preferably by esterification in the presence of a strong acid, such as concentrated sulfuric acid, with the desired alkanol.

Conversely, if any of the above-described methods yields a compound of the formula I wherein $R_4$ is alkyl, this ester group may readily be split off by acid or alkaline hydrolysis. For instance, the free acid may be obtained by briefly heating the ester with methanolic potassium hydroxide, and acidifying the reaction mixture.

Finally, those compounds of the formula I wherein $R_4$ is hydrogen may, is desired, be converted by conventional methods into non-toxic, pharmacologically acceptable alkali metal or alkaline earth metal salts or addition salts with an organic base, such as cyclohexylamine, isobutylamine, morpholine, ethanolamine, diethanolamine, dimthylaminoethanol or the like.

The following examples further illustrate the present invention and will enable others skilled in the art to understand it more completely. It should be understood, however, that the invention is not limited solely to the particular examples given below.

PREPARATION OF A STARTING COMPOUND OF THE FORMULA III

EXAMPLE A

Ethyl 4-(4'-fluoro-4-biphenylyl)-4-oxo-crotonate a. 44 gm (0.33 mol) of aluminum chloride were added in small portions to a solution of 51.7 gm (0.3 mol) of 4-fluoro-biphenyl and 66.6 gm (0.33 mol) of bromoacetyl bromide in 150 cc of ethylene chloride, while cooling the solution on an ice-salt bath, and the mixture was then stirred at room temperature for two hours. Thereafter, the reaction mixture was admixed with ice and hydrochloric acid, and the organic phase was separated, washed with water, dried with sodium sulfate and evaporated. The residue was recrystallized from 250 cc of carbon tetrachloride, yielding 53 gm (60% of theory) of 2-bromo-4'-4-fluoro-phenyl)-acetophenone, m.p. 102°–103° C.

b. A mixture of 18.5 gm (0.0538 mol) of triphenyl-carbethoxy-methylenephosphoran and 260 cc of absolute benzene was heated to boiling, 7.6 gm (0.026 mol) of 2-bromo-4'-(4-fluoro-phenyl)-acetophenone were added, and the mixture was stirred for two hours at the boiling point. Thereafter, the precipitated triphenyl-carbethoxy-methylphosphonium bromide was separated by vacuum filtration, the clear filtrate was admixed with 4.35 gm (0.026 mol) of ethyl bromoacetate to tie up the triphenyl-phosphine, and the mixture was again boiled for two hours. Thereafter, the reaction mixture was allowed to cool, was then filtered, the filtrate was evaporated, and the residue was recrystallized first from methanol and subsequently from cyclohexane, yielding 4.2 gm (54% of theory) of the compound of the formula

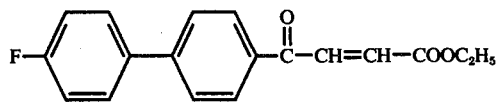

having a melting point of 115°–117° C.

PREPARATION OF END PRODUCTS OF THE FORMULAS I AND Ia

EXAMPLE 1

4-(4'-Fluoro-4-biphenylyl)-butyric acid by method A 5.0 gm (0.018 mol) of 4-(4'-fluoro-4-biphenylyl)-4-oxo-butyric acid were hydrogenated in 50 ml of acetic acid under addition of 1.5 ml of perchloric acid in the presence of 1.5 gm of palladium/barium sulfate (5%) as catalyst at room temperature and at a pressure of 5 atmospheres in a Parr-autoclave.

After absorption of the calculated quantity of hydrogen, the catalyst was vacuum-filtered off and the solvent was removed in vacuo. The residue was admixed with water, vacuum-filtered off and washed with water. For further purification, the reaction product was dissolved in ether, and the solution was filtered through charcoal, dried and the solvent was removed. After recrystallization from cyclohexane, 4-(4'-fluoro-4-biphenylyl)-butyric acid, m.p. 119°–120° C, was obtained. Yield: 4.0 gm (62.2% of theory). Melting point of the cyclohexylamine salt: 175°–176° C (precipitated from ethyl acetate and recrystallized from ethyl acetate/ethanol).

EXAMPLE 2

4-4'-Chloro-4-biphenylyl)-butyric acid by method A

A solution of 12.3 gm (42.7 millimols) of 4-(4'-chloro-4-biphenylyl)-4-oxo-butyric acid in 150 ml of acetic acid was admixed with 4 ml of orthophosphoric acid of 89% and hydrogenated in the presence of 4 gm of palladium/barium sulfate (5%) at a hydrogen pressure of 5 atmospheres and at room temperature. The catalyst was vacuum-filtered off, and the solvent was evaporated. The residue was dissolved in ether, the organic phase was washed with water and evaporated to dryness. The free acid thus obtained was dissolved again in ethyl acetate, the solution was filtered and mixed with a small excess of cyclohexylamine. Yield: 9.5 gm (62.5% of theory); m.p. 187°–190° C (cyclohexylamine salt). Melting point of the free acid: 136°–137° C.

EXAMPLE 3

4-(2',4'-Difluoro-4-biphenylyl)-butyric acid

Prepared analogous to Example 1 from 4-(2',4'-difluoro-4-biphenylyl)-4-oxo-butyric acid. Yield: 39% of theory; m.p. 76°–77° C (from cyclohexane). Melting point of the cyclohexylamine salt: 127°–128° C (from ethyl acetate/methanol 9:1).

EXAMPLE 4

4-(2'-Chloro-4'-fluoro-4-biphenylyl)-butyric acid

Prepared analogous to Example 1 from 4-(2'-chloro-4'-fluoro-4-biphenylyl)-4-oxo-butyric acid. Yield: 84% of theory; m.p. 81°–82° C (petroleum ether-cyclohexane). Melting point of the cyclohexylamine salt: 148°–149° C (from ethyl acetate/methanol 9:1).

EXAMPLE 5

4-(2'-Fluoro-4'-chloro-4-biphenylyl)-butyric acid

Prepared analogous to Example 1 from 4-(2'-fluoro-4'-chloro-4-biphenylyl)-4-oxo-butyric acid. yield: 60% of theory. Melting point of the cyclohexylamine salt: 134°–136° C (from isopropanol).

EXAMPLE 6

4-(3',4'-Dichloro-4-biphenylyl)-butyric acid

Prepared analogous to Example 1 from 4-(3',4'-dichloro-4-biphenylyl)-4-oxo-butyric acid. Yield: 62% of theory. Melting point of the cyclohexylamine salt: 167°–168° C (from isopropanol).

EXAMPLE 7

4-(2'-Amino-4-biphenylyl)-butyric acid by method A 6 gm (0.02 mol) of 4-(2'-nitro-4-biphenylyl)-4-oxo-butyric acid were hydrogenated in 60 ml of acetic acid and 2.5 ml of perchloric acid in the presence of 2.5 gm of palladium/barium sulfate (5%) as catalyst at room temperature and at a pressure of 5 atmospheres in a Parr-autoclave. After absorption of the calculated quantity of hydrogen, the catalyst was vacuum-filtered off, and the solvent was removed in vacuo. The residue was dissolved in water and admixed with ether. By addition of sodium bicarbonate solution, the aqueous phase was adjusted to a pH-value of about 5. Now, the ether solution was separated, washed with water and the solvent was removed. The obtained 4-(2'-amino-4-biphenylyl)-butyric acid was dissolved in ether and mixed with cyclohexylamine; the precipitated cyclohexylamine salt was collected and recrystallized from methylene chloride and then from acetone/ether. Melting point 123°–126° C.

EXAMPLE 8

4-(2'-Chloro-4-biphenylyl)-butyric acid by method A

A solution of 17.8 gm (59 millimols) of methyl 4-(2'-chloro-4-biphenylyl)-4-oxo-butyrate in 150 ml of anhydrous acetic acid was admixed with 4 ml of perchloric acid of 70% and hydrogenated in the presence of 4 gm of palladium/barium sulfate (5%) at 5 atmospheres and at room temperature for 8 hours. The catalyst was vacuum-filtered off and the solvent was removed in vacuo; the residue was taken up in water and ethylene chloride. The carboxylic acid obtained from the separated organic phase was extracted with potassium carbonate and precipitated by acidifying. The free acid was extracted with ether, the ethereal solution was dried and distilled in a high vacuum (b.p. 186°–190° C at 0.08 mm Hg). Yield: 62% of theory; m.p. 61.5°–63° C (from cyclohexane/benzene). Melting point of the cyclohexylamine salt: 140° C (from isopropanol).

From the ethylenechloride solution methyl 4-(2'-chloro-4-biphenylyl)-butyrate, b.p. 153° C at 0.06 mm Hg, was obtained, which may be hydrolized with alkali to the above-mentioned carboxylic acid.

EXAMPLE 9

4-(2'-Chloro-4-biphenylyl)-butyric acid 18.6 gm of 4-(2'-chloro-4-biphenylyl)-4-hydroxybutyric acid (obtained by acidifying 20 gm of its sodium salt and extraction with ethyl acetate) were hydrogenated in 200 ml of glacial acetic acid in the presence of 2 ml of perchloric acid and in the presence of palladium/barium sulfate (5%) at room temperature and at a hydrogen pressure of 5 atmospheres. After filtration, the solvent was evaporated and the residue admixed with water; the crystalline acid was collected and dried. Yield: 70% of theory; m.p. 60°–61° C (from petroleum ether). Melting point of the cyclohexylamine salt: 143°–144° C (from water).

EXAMPLE 10

4-(2'-Fluoro-4-biphenylyl)-butyric acid by method A 13.7 gm (0.05 mol) of 4-(2'-fluoro-4-biphenylyl)-4-oxo-crotonic acid in 100 ml of glacial acetic acid and 2 ml of perchloric acid were hydrogenated in the presence of 4 gm of 5% palladium/barium sulfate at room temperature and at atmospheric pressure; the reaction was finished after absorption of 3 mols of hydrogen. After filtering, the mixture was evaporated in vacuo, the residue distributed between water and ethyl acetate and the ethyl acetate phase was evaporated. The residue was crystallized from cyclohexane. Yield: 11.1 gm (61.4% of theory); m.p. 65°–66° C. Melting point of the cyclohexylamine salt: 130°–132° C. Melting point of the sodium salt: 139°–141° C. Melting point of the isobutylamine salt: 92°–93° C (from ethyl acetate).

EXAMPLE 11

4-(2',4'-Dichloro-4-biphenylyl)-butyric acid

Prepared analogous to Example 9 from 4-(2',4'-dichloro-4-biphenylyl)-4-hydroxy-butyric acid. Melting point of the cyclohexylamine salt: 154°–155° C (from water).

EXAMPLE 12

4-(4'-Fluoro-4-biphenylyl)-butyric acid 15 ml of water, 35 ml of concentrated hydrochloric acid, 50 ml of toluene and 10 gm of 4-(4'-fluoro-4-biphenylyl)-4-oxo-butyric acid were added to 20 gm of amalgamated zinc (Org. Synthesis, Coll. Vol. III, 786), and the mixture was refluxed for 6 hours while stirring, another 10 ml of concentrated hydrochloric acid being added after 3 hours. Subsequently, the mixture was vacuum-filtered to remove the unreacted zinc, and the filtrate was extracted with ether. The residue remaining after evaporation of the ether was recrystallized from cyclohexane, yielding 7.5 gm (79% of theory) of colorless 4-(4'-fluoro-4-biphenylyl)-butyric acid, m.p. 118°–120° C.

EXAMPLE 13

4-(2'-Bromo-4-biphenylyl)-butyric acid by method A

A mixture of 6.6 gm (0.018 mol) of ethyl 4-(2'-bromo-4-biphenylyl)-4-oxo-butyrate (m.p. 61°–62° C), 3 gm of 100% hydrazine hydrate and 100 ml of diethyleneglycol was heated at 100° C for 20 minutes. Then, 5 gm of pulverized potassium hydroxide were added. After refluxing for 5 hours, the reaction mixture was poured into 500 ml of water, acidified with dilute hydrochloric acid, and the precipitate was dissolved in ether. The ether solution was washed with water, dried and evaporated; the residue was dissolved in acetone, and by addition of cyclohexylamine the cyclohexylamine salt of 4-(2'-bromo-4-biphenylyl)-butyric acid, m.p. 148°–149° C (from acetone), was obtained. Melting point of the free acid: 63° C (from cyclohexane).

EXAMPLE 14

4-(4'-Bromo-4-biphenylyl)-butyric acid

Prepared analogous to Example 13 from ethyl 4-(4'-bromo-4-biphenylyl)-4-oxo-butyrate (m.p. 116°–117° C). Melting point of 4-(4'-bromo-4-biphenylyl)-butyric acid: 140° C. Yield: 86% of theory. Melting point of the cyclohexylamine salt: 187° C.

EXAMPLE 15

4-(4'-Fluoro-4-biphenylyl)-butyric acid by method A 1.50 gm (0.005 mol) of the sodium salt of 4-(4'-fluoro-4-biphenylyl)-4-hydroxy-butyric acid were refluxed in 15 ml of glacial acetic acid and 25 ml of hydroiodic acid ($d$=2.00) for 10 hours, and then the reaction mixture was poured into a solution of 5 gm of sodium bisulfite in 400 ml of water. The colorless precipitate was collected and recrystallized from cyclohexane, yielding 4-(4'-fluoro-4-biphenylyl)-butyric acid, m.p. 119°–120° C. Melting point of the cyclohexylamine salt: 177° C (precipitated from ethyl acetate). Yield: 1.3 gm.

EXAMPLE 16

4-(2'-Fluoro-4-biphenylyl)-butyric acid by method A 1.10 gm (0.004 mol) of 4-(2'-fluoro-4-biphenylyl)-4-oxo-crotonic acid were refluxed while stirring, in 10 ml of glacial acetic acid and 20 ml hydroiodic acid ($d$=2.00) for 12 hours. Subsequently, the solution was poured into 200 ml of water, the aqueous mixture was decolorized with sodium bisulfite, and extracted twice with 100 ml of ether each. The ether solution was washed with water and evaporated; the solid residue was refluxed with 150 ml of cyclohexane, the undissolved starting material was vacuum-filtered off, and the cyclohexane solution was evaporated to dryness. The residue was dissolved in 20 ml of ethyl acetate, and by addition of cyclohexylamine the cyclohexylamine salt of 4-(2'-fluoro-4-biphenylyl)-butyric acid was precipitated; m.p. 132°–134° C, after recrystallization from ethyl acetate/ethanol. Yield: 0.60 gm.

EXAMPLE 17

4-(2'-Fluoro-4'-amino-4-biphenylyl)-butyric acid

Prepared analogous to Example 7 from 4-(2'-fluoro-4'-nitro-4-biphenylyl)-4-oxo-butyric acid. Melting point of the hydrochloride: 170° C (decomp.).

EXAMPLE 18

4-(4'-Nitro-4-biphenylyl)-butyric acid by method B

To a suspension of 14.4 gm of 4-(4-biphenylyl)-butyric acid in 72 ml of glacial acetic acid at 24°–27° C 24 ml of fuming nitric acid ($d$=1.52) were added dropwise. After stirring for 5 minutes, the mixture was poured into ice water while stirring, and the aqueous mixture was extracted with benzene. The benzene phase was washed with water, dried and evaporated; the residue was dissolved in 100 ml of acetone and admixed with 6.8 ml of cyclohexylamine. The thus obtained cyclohexylamine salt had a melting point of 160°–161° C (after recrystallization from 200 ml of isopropanol). Melting point of the free acid: 124° C (from carbon tetrachloride).

EXAMPLE 19

4-(4'-Amino-4-biphenylyl)-butyric acid by method A

A mixture of 4 gm of 4-(4-amino-4-biphenylyl)-4-oxo-butyric acid, 240 ml of glacial acetic acid and 1 ml of perchloric acid was hydrogenated in the presence of 1 gm of palladium/barium sulfate as catalyst at 40° C and at a pressure of 5 atmospheres. After absorption of the calculated quantity of hydrogen, the catalyst was vacuum-filtered off, and the solvent was removed in vacuo. The residue was dissolved in ethyl acetate while warming, and the ethyl acetate solution was then washed with water, dried and evaporated. The thus obtained 4-(4'-amino-4-biphenylyl)-butyric acid, dissolved in ethyl acetate, was converted into its cyclohexylamine salt by addition of cyclohexylamine. Yield: 4 gm; melting point of the cyclohexylamine salt: 188°–190° C.

EXAMPLE 20

4-(4'-Chloro-2'-methyl-4-biphenylyl)-butyric acid

Prepared analogous to Example 1 by reduction of 4-(4'-chloro-2'-methyl-4-biphenylyl)-4-oxo-butyric acid. Yield: 76%. Melting point of the cyclohexylamine salt: 145.5°–147° C (from ethyl acetate).

EXAMPLE 21

4-(4'-Amino-3'-bromo-4-biphenylyl)-butyric acid by method A

A mixture of 6 ml of water, 8 gm of amalgamated zinc, 14 ml of concentrated hydrochloric acid, 20 ml of toluene and 4 gm of 4-(4'-amino-3'-bromo-4-biphenylyl)-4-oxo-butyric acid was refluxed for 6 hours, while stirring. Subsequently, 10 ml of dioxane were added and the toluene/dioxane phase was separated. The residue remaining after evaporation of the solvent was admixed with water, covered with ether, and adjusted with sodium bicarbonate solution to pH 6. The ether solution was separated, washed with water, dried over sodium sulfate and evaporated. The thus obtained 4-(4'-amino-3'-bromo-4-biphenylyl)-butyric acid was dissolved in ethyl acetate and converted into its cyclohexylamine salt by addition of cyclohexylamine. Yield: 25% of theory. Melting point of the cyclohexylamine salt: 182° C (decomp.).

EXAMPLE 22

4-(4'-Acetamido-3'-bromo-4-biphenylyl)-butyric acid by method A 7.5 ml of water, 17.5 ml of concentrated hydrochloric acid, 50 ml of toluene, 30 ml of dioxane and 5 gm of 4-(4'-acetamido-3'-bromo-4-biphenylyl)-4-oxo-butyric acid were added to 10 gm of amalgamated zinc. This reaction mixture was refluxed for 4 hours. After standing overnight at room temperature, the precipitated crystals were collected and recrystallized from ethyl acetate. Yield: 35% of theory; m.p. 155°–156° C. Melting point of the cyclohexylamine salt: 179°–180° C (precipitated from ethyl acetate).

EXAMPLE 23

4-(3'-Chloro-4-biphenylyl)-butyric acid

Prepared analogous to Example 9 from 4-(3'-chloro-4-biphenylyl)-4-hydroxy-butyric acid. Melting point of the cyclohexylamine salt: 147°–148° C Yield: 41% of theory.

EXAMPLE 24

4-(2',3'-Dichloro-4-biphenylyl)-butyric acid

Prepared analogous to Example 12 from 4-(2',3'-dichloro-4-biphenylyl)-4-oxo-butyric acid. Yield: 97% of theory, m.p. 70°–71° C (from petroleum ether/cyclohexane); melting point of the cyclohexylamine salt: 163°–165° C.

EXAMPLE 25

4-(2'-Fluoro-4-biphenylyl)-4-hydroxy-butyric acid by method C 45.9 gm (0.169 mol) of 4-(2'-fluoro-4-biphenylyl)-4-oxo-butyric acid were dissolved in a solution of 11.2 gm of potassium hydroxide in 450 ml of water at 35° C. While stirring, a solution of 6.4 gm (0.169 mol) of sodium borohydride in water was added. After stirring for about 3 hours, the mixture was acidified and extracted with ethyl acetate. From the washed and dried organic phase, the cyclohexylamine salt was precipitated by addition of cyclohexylamine. Yield: 41 gm (65% of theory); m.p. 174°–175° C; melting point of the free acid: 120°–122° C (from benzene); melting point of the isobutylamine salt: 125°–127° C (from isopropanol); melting point of the morpholine salt: 108°–110° C (from isopropanol); melting point of the sodium salt: 222°–224° C (from ethanol).

EXAMPLE 26

4-(2'-Chloro-4-biphenylyl)-4-hydroxy-butyric acid

Prepared analogous to example 25 example from 4-(2'-chloro-4-biphenylyl)-4-oxo-butyric acid. Yield: 55% of theory. Melting point of the cyclohexylamine salt: 157°–158° C (from water); melting point of the isobutylamine salt: 131°–133° C (from isopropanol); the sodium salt has a double melting point of 90°–95° C and 130°–133° C (from ethanol).

EXAMPLE 27

4-(2'-Bromo-4-biphenylyl)-4-hydroxy-butyric acid

Prepared analogous to Example 25 from 4-(2'-bromo-4-biphenylyl)-4-oxo-butyric acid. Melting point of the cyclohexylamine salt: 162°–163° C; yield: 53.4% of theory.

EXAMPLE 28

4-(4'-Fluoro-4-biphenylyl)-4-hydroxy-butyric acid

Prepared analogous to Example 25 from 4-(4'-fluoro-4-biphenylyl)-4-oxo-butyric acid. Melting point of the cyclohexylamine salt: 175°–177° C (from water). Yield 54% of theory.

EXAMPLE 29

4-(4'-Chloro-4-biphenylyl)-4-hydroxy-butyric acid

Prepared analogous to Example 25 from 4-(4'-chloro-4-biphenylyl)-4-oxo-butyric acid. Melting point of the cyclohexylamine salt: 185°–186° C (from water). Yield: 61% of theory.

EXAMPLE 30

4-(4'-Bromo-4-biphenylyl)-4-hydroxy-butyric acid

Prepared analogous to Example 25 from 4-(4'-bromo-4-biphenylyl)-4-oxo-butyric acid. Yield: 70% of theory; m.p. 127° C. Melting point of the cyclohexylamine salt: 193° C.

EXAMPLE 31

4-(2',4'-Difluoro-4-biphenylyl)-4-hydroxy-butyric acid

Prepared analogous to Example 25 from 4-(2',4'-difluoro-4-biphenylyl)-4-oxo-butyric acid. Melting point 111°–112.5° C (from cyclohexane/ethyl acetate 4:1); melting point of the cyclohexylamine salt: 160°–161° C (from acetone/ethyl acetate 1:2).

EXAMPLE 32

4-(2'-Chloro-4'-fluoro-4-biphenylyl)-hydroxy-butyric acid

Prepared analogous to Example 25 from 4-(2'-chloro4'-fluoro-4-biphenylyl)-4-oxo-butyric acid. Melting point 78°–79° C (from benzene/petroleum ether 3:2); melting point of the cyclohexylamine salt: 161°–162° C (from ethyl acetate/methanol 1:1).

EXAMPLE 33

4-(2'-Fluoro-4'-chloro-4-biphenylyl)-4-hydroxy-butyric acid

Prepared analogous to Example 25 from 4-(2'-fluoro-4'-chloro-4-biphenylyl)-4-oxo-butyric acid. Yield: 69% of theory; m.p. of the cyclohexylamine salt: 165°–167° C (from isopropanol).

EXAMPLE 34

4-(2'-Nitro-4-biphenylyl)-4-hydroxy-butyric acid

Prepared analogous to Example 25 from 4-(2'-nitro-4-biphenylyl)-4-oxo-butyric acid. Yield: 62.5% of theory; m.p. 114°–115° C; melting point of the cyclohexylamine salt; 170° C (decomp.).

EXAPLE 35

4-(4'-Nitro-4-biphenylyl)-4-hydroxy-butyric acid

Prepared analogous to Example 25 from 4-(4'-nitro-4-biphenylyl)-4-oxo-butyric acid. Yield: 45% of theory; m.p. 153° C (decomp.); melting point of the cyclohexylamine salt: 178°–179° C (decomp.).

EXAMPLE 36

4-(4'-Chloro-2'-nitro-4-biphenylyl)-4-hydroxy-butyric acid

Prepared analogous to Example 25 from 4-(4'-chloro-2'-nitro-4-biphenylyl)-4-oxo-butyric acid. Yield: 46% of theory. Melting point of the cyclohexylamine salt: 171°–172° C (from isopropanol).

EXAMPLE 37

4-(2'-Nitro-4'-methyl-4-biphenylyl)-4-hydroxy-butyric acid

Prepared analogous to Example 25 from 4-(2'-nitro-4'-methyl-4-biphenyl)-4-oxo-butyric acid. Yield: 68% of theory. Melting point of the cyclohexylamine salt: 156°–157° C (from isopropanol).

EXAMPLE 38

4-(5'-Chloro-2'-methyl-4-biphenyl)-4-hydroxy-butyric acid

Prepared analogous to Example 25 from 4-(5'-chloro-2'-methyl-4-biphenylyl)-4-oxo-butyric acid. Yield: 90% of theory. Melting point of the cyclohexylamine salt: 114°–115° C (from ethyl acetate).

EXAMPLE 39

4-(3'-Nitro-4-biphenylyl)-4-hydroxy-butyric acid

Prepared analogous to Example 25 from 4-(3'-nitro-4-biphenylyl)-4-oxo-butyric acid Yield: 41% of theory. Melting point of the cyclohexylamine salt: 161°–162° C (from isopropanol).

EXAMPLE 40

γ-(2'-Fluoro-4-biphenylyl)-γ-butyrolactone and 4-(2'-fluoro-4-biphenyl)-4-hydroxy-butyric acid by method D A mixture of 9 gm (0.03 mol) of ethyl 4-(2'-fluoro-4-biphenylyl)-4-oxo-butyrate, 150 ml of absolute isopropanol and 6.2 gm (0.03 mol) of freshly distilled aluminum isopropylate was refluxed on a boiling water bath, while condensing the vapors in a descending condenser, until no more acetone was detectable in the distillate. After removing the solvent in vacuo, the residue was covered with ether, the mixture was acidified with dilute hydrochloric acid, and the ethereal phase was separated, washed with sodium bicarbonate and water. After distilling off the solvent, the solid residue was recrystallized from cyclohexane, to yield 6 gm (78% of theory) of colorless γ-(2'-fluoro-4-biphenylyl)-γ-butyrolactone, m.p. 74°–75° C.

1 gm (0.0039 mol) of the lactone was heated for 10 minutes on a boiling water bath with 10 ml of ethanol and 10 ml of aqueous 20% sodium hydroxide, and then the mixture was diluted with 200 ml of water and acidified with 20% formic acid; the precipitated 4-(2'-fluoro-4-biphenylyl)-4-hydroxybutyric acid had a melting point of 119°–120° C. The mixed melting point with the acid prepared in Example 25 showed no depression. Melting point of the cyclohexylamine salt: 173°–174° C (decomp., precipitated from ethyl acetate).

EXAMPLE 41

γ-(4'-Fluoro-4-biphenylyl)-γ-butyrolactone

Melting point 135°–137° C and therefrom:

4-(4'-Fluoro-4-biphenylyl)-4-hydroxy-butyric acid

Melting point of the cyclohexylamine salt: 174°–176° C Prepared analogous to Example 40 from methyl 4-(4'-fluoro-4-biphenylyl)-4-oxo-butyrate.

EXAMPLE 42

4-(4'-Fluoro-4biphenylyl)-4-hydroxy-butyric acid by method C 5.0 gm (0.0184 mol) of 4-(4'-fluoro-4-biphenylyl)-4-oxo-butyric acid were hydrogenated in a solution of 0.81 gm (0.0202 mol) of a sodium hydroxide in 200 ml of water at room temperature and at a hydrogen pressure of 5 atmospheres in the presence of 1.5 gm of 5% palladium/barium sulfate. After completion of the hydrogen absorption, the crystals which had precipitated were redissolved by heating, and then the catalyst was vacuum-filtered off. The free acid was obtained by acidifying the filtrate; by adding cyclohexylamine to a solution of the acid in acetone, the corresponding cyclohexylamine salt, m.p. 175°–176° C, was obtained. Yield: 4.7 gm (68.5% of theory).

EXAMPLE 43

4-(4'-Fluoro-4-biphenyl)-4-hydroxy-butyric acid by method C

To a solution of 2.75 gm (0.01 mol) of 4-(4'-fluoro-4-biphenylyl)-4-oxo-butyric acid in 50 ml of absolute tetrahydrofuran 0.20 gm (0.005 mol) of lithiumaluminumhydride in 50 ml of absolute tetrahydrofuran was added dropwide, while stirring and cooling at −20° C. After stirring for 4 hours at −20° C, the reaction mixture was poured into ice water and acidified with aqueous 50% sulfuric acid. Subsequently, the mixture was made alkaline by adding aqueous 20% sodium hydroxide, and was again acidified with formic acid. The precipitated semi-solid product was dissolved in ether, and after evaporating the ether, the crystalline residue was dissolved in acetone. From this solution the cyclohexylamine salt of 4-(4'-fluoro-4-biphenylyl)-4-hydroxy-butyric acid was precipitated by addition of cyclohexylamine, and the salt was recrystallized from ethyl acetate/absolute ethanol. Melting point 176°–178° C (decomp.); yield: 2.2 gm.

EXAMPLE 44

4-(2'-Fluoro-4-biphenyl)-4-hydroxy-butyric acid by method C

To a boiling solution of 3.14 gm (0.01 ml) of propyl 4-(2'-fluoro-4-biphenylyl)-4-oxo-butyrate in 150 ml of 90% ethanol 0.69 gm (0.03 gm-atom) of metallic sodium was added in small portions over a period of 90 minutes, while stirring. After the metallic sodium had dissolved, 400 ml of water were added to the mixture. After acidifying with hydrochloric acid, the mixture was extracted with ether and the ethereal phase was dried and evaporated, leaving the desired acid as a residue. Melting point of the cyclohexylamine salts: 174°–175° C (from ethanol).

EXAMPLE 45

4-(2',4'-Dichloro-4-biphenylyl)-4-hydroxy-butyric acid

Prepared analogous to Example 42 from 4-(2',4'-dichloro-4-biphenylyl)-4-oxo-butyric acid. Yield: 70% of theory. Melting point of the cyclohexylamine salt: 168°–169° C (from water).

EXAMPLE 46

4-(4'-Chloro-2'-cyano-4-biphenylyl)-4-hydroxy-butyric acid by method D 9.90 gm (0.0316 mol) of 4-(4'-chloro-2'-cyano-4-biphenylyl)-4-hydroxy-crotonic acid in 500 ml of dry ethyl acetate were hydrogenated in the presence of 2.50 gm of Raney nickel, at a hydrogen pressure of 5 atmospheres and at room temperature until the end of hydrogen absorption. After filtering, the filtrate was washed twice with 100 ml of 1% hydrochloric acid each and then with water, dried over sodium sulfate and evaporated in vacuo. The oily, yellowish residue was dissolved in ethyl acetate and converted into the cyclohexylamine salt by addition of the equimolar quantity of cyclohexylamine. Yield: 6.15 gm; m.p. 168°–169° C (from acetone/ethyl acetate 1:1).

EXAMPLE 47

4-(3',4'-Dichloro-4-biphenylyl)-4-hydroxy-butyric acid

Prepared analogous to Example 46 from the sodium salt of the 4-(3',4'-dichloro-4-biphenylyl)-4-hydroxy-crotonic acid in methanol. Yield: 62% of theory. Melting point of the cyclohexylamine salt: 158°–159° C (from water).

EXAMPLE 48

4-(2-Chloro-4-biphenylyl)-4hydroxy-butyric acid 4-hydroxy-butyric acid

Prepared analogous to Example 42 from 4-(2-chloro-4-biphenylyl)-4-oxo-butyric acid. Melting point 87°–88° C (from cyclohexane/ether); melting point of the cyclohexylamine salt: 156°–157° C (from acetone/ethyl acetate).

EXAMPLE 49

4-(2'-Amino-4-biphenylyl)-4-hydroxy-butyric acid 6 gm (0.02 mol) of 4-(2'-nitro-4-biphenylyl)-4-hydroxy-butyric acid (m.p. 114°–115° C) were hydrogenated in 60 ml of methanol in the presence of 0.6 gm of platinum dioxide as a catalyst, at room temperature and atmospheric pressure. After absorption of the calculated quantity of hydrogen, the catalyst was vacuum-filtered off, and the solvent was distilled off. The residue, which solidified after some time, was recrystallized from methanol, yielding 4-(2'4-biphenylyl),4-hydroxy-butyric acid, m.p. 102°–103° C. Melting point of the cyclohexylamine salt: 157°–158° C (decomp,; precipitated from ethyl acetate and recrystallized from ethyl acetate/isopropanol).

EXAMPLE 50

4-(2'-Fluoro-4'-nitro-4-biphenylyl)-4-hydroxy-butyric acid and
γ-(2'-fluoro-4'-nitro-4-biphenylyl)-γ-butyrolactone Prepared analogous to Example 40, but using as starting material 4-(2'-fluoro-4'-nitro-biphenylyl)-4-oxo-butyric acid. 4-(2'-fluoro-4'nitro-4-biphenylyl)-4-hydroxy-butyric acid was isolated as its cyclohexylamine salt (m.p. 152°–153° C, decomp.), which was precipitated from the solution of the acid in ethyl acetate by addition of cyclohexylamine. After evaporation of the ethyl acetate filtrate, the residue was recrystallized from cyclohexane/ethyl acetate, yielding γ-(2'-fluoro-4'-nitro-4-biphenylyl)-γ-butyrolactone of m.p. 94° C.

EXAMPLE 51

4-(4'-Amino-4-biphenylyl)-4-hydroxy-butyric acid by method E 6 gm (0.02 mol) of 4-(4'-nitro-4-biphenylyl)-4hydroxy-butyric acid in 200 ml of methanol were hydrogenated in the presence of 3 gm of Raney nickel as a catalyst, at room temperature and at a pressure of 5 atmospheres. After absorption of the calculated quantity of hydrogen, the catalyst was vacuum-filtered off and the solvent was distilled off. The residual 4-(4'-amino-4-biphenylyl)-4-hydroxy-butyric acid, after recrystallization from methanol, had a m.p. of 145° C (decomp.). Melting point of the cyclohexylamine salt: 178° C (decomp.; precipitated from ethyl acetate/absolute ethanol). Yield: 5.5 gm.

EXAMPLE 52

4-(3',4'-Difluoro-4-biphenylyl)-4-hydroxy-butyric acid

Prepared analogous to Example 46 from the morpholine salt of 4-(3',4'-difluoro-4-biphenylyl)-4-hydroxy-crotonic acid in methanol. Melting point of the cyclohexylamine salt: 170°–171° C (from water). Yield: 44% of theory.

EXAMPLE 53

4-(2'-Chloro-4-biphenylyl)-4-hydroxy-butyric acid

A mixture of 5.44 gm (0.02 mol) of γ-(2'-chloro-4-biphenylyl)-γ-butyrolactone (b.p. 212°–213° C at 0.03 mm Hg), 50 ml of methanol, 1 gm of sodium hydroxide and 2 ml of water was boiled for 2 hours. The reaction mixture was then evaporated, the residue was distributed between dilute hydrochloric acid and ethyl acetate, and the cyclohexylamine salt was precipitated from the washed and dried ethyl acetate solution. Yield: 5.8 gm m.p. of the cyclohexylamine salt: 158°–159° C (from water).

EXAMPLE 54

4-(4'-Chloro-2'-methyl-4-biphenylyl)-4-hydroxy-butyric acid

Prepared analogous to Example 25 by reduction of 4-(4'-chloro-2'-methyl-4-biphenylyl)-4-oxo-butyric acid (m.p. 153°–154° C) with sodium borohydride. Yield: 96%. Melting point of the cyclohexylamine salt: 139°–140° C (from ethylene chloride/ethyl acetate 5:1).

EXAMPLE 55

4-(4'-Amino-3'-bromo-4-biphenylyl)-4-hydroxy-butyric acid

Prepared analogous to Example 25 by reduction of 4-(4'-amino-3'-bromo-4-biphenyly)-4-oxo-butyric acid. Yield: 67%; m.p. 112°–113° C (decomp.). Melting point of the cyclohexylamine salt: 183° C.

EXAMPLE 56

4-(2'-Cyano-4-biphenylyl)-4-hydroxy-butyric acid

Prepared analogous to Example 25 from 4-(2'-cyanobiphenylyl)-4-oxo-butyric acid. Melting point of the cyclohexylamine salt: 167°–168° C (from ethyl acetate by addition of 15% methanol). Yield: 94% of theory.

EXAMPLE 57

4-(3'-Chloro-4-biphenylyl)-4-hydroxy-butyric acid

Prepared analogous to Example 25 from 4-(3'-chloro-4-biphenylyl)-4-oxo-butyric acid. Melting point of the cyclohexylamine salt: 160°–161° C (from ethyl acetate by addition of methanol). Yield: 65% of theory.

EXAMPLE 58

4-(2',3'-Dichloro-4-biphenylyl)-4-hydroxy-butyric acid

Prepared analogous to Example 25 from 4-(2',3'-dichloro-4-biphenylyl)-4-oxo-butyric acid. Yield: 75% of theory, m.p. 134°–135° C (decomp.). Melting point of the cyclohexylamine salt: 158° C (decomp.).

EXAMPLE 59

4-(2'-Acetamido-4-biphenylyl)-4-hydroxy-butyric acid

Prepared analogous to Example 25 from 4-(2'-acetamido-4-biphenylyl)-4-oxo-butyric acid (m.p. 209°–210° C). Melting point of the cyclohexylamine salt: 143° C; melting point of the isobutylamine salt: 125°–126° C; yield: 60% of theory.

EXAMPLE 60

4-(4'-Acetamido-3'-bromo-4-biphenylyl)-4-hydroxy-butyric acid

Prepared analogous to Example 25 from 4-(4'-acetamino-3'-bromo-4-biphenylyl)-4-oxo-butyric acid. Yield: 53% of theory, m.p. 125°–126° C. Melting point of the cyclohexylamine salt: 165°–167° C (from ethanol).

EXAMPLE 61

4-(2-Fluoro-4-biphenylyl)-4-hydroxy-butyric acid

Prepared analogous to Example 25 from 4-(2-fluoro-4-biphenylyl)-4-oxo-butyric acid. Yield: 74% of theory, m.p. 133°–135° C (from benzene).

EXAMPLE 62

Ethyl 4-(2'-fluoro-4-biphenylyl)-4-hydroxy-butyrate

To a solution of 15 gm (0.05 mol) of ethyl 4-(2'-fluoro-4-biphenylyl)-4-oxo-butyrate in 100 ml of methanol 1.9 gm (0.05 mol) of sodium borohydride were added at a temperature between 0° and 5° C, while stirring. The precipitate was vacuum-filtered off and dissolved in ether. The ethereal solution was washed with an aqueous sodium bicarbonate solution and then with water, dried and evaporated. The residual oil was recrystallized from cyclohexane. Yield: 12 gm (79.5% of theory), m.p. 61°–62° C.

EXAMPLE 63

Methyl 4-(2'-fluoro-4-biphenylyl)-butyrate 13.3 gm (0.049 mol) of 4-(2'-fluoro-biphenylyl)-4-hydroxy-crotonic acid were hydrogenated in 100 ml of methanol in the presence of 1 gm of 10% palladized charcoal at room temperature and atmospheric pressure. After filtering, the mixture was evaporated, and the oily residue was chromatographically purified on 360 gm of silicagel (0.05–0.02 mm grain size, activity stage (1) with benzene/ethyl acetate (2/1), 5.4 gm of the ester (oil), $R_f$-value 0.8 [silicagel plates benzene/ethyl acetate (2/1)] were obtained.

The compounds according to the present invention, that is, those embraced by formulas I and Ia above and their non-toxic salts, have useful pharmacodynamic properties. More particularly, the compounds of the instant invention exhibit antiphlogistic, analgestic, antitussive and thrombocyte aggregation inhibiting activities in warm-blooded animals, such as mice and rats. With respect to the antiphlogistic activity, the compounds according to the present invention are significantly superior to known antiphlogistics of similar structure and that their antiphlogistic action is of exceptionally long duration.

The antiphlogistic activity of the compounds of the present invention was ascertained by the standard test method Hillebrecht described in Arzneimittelforschung 4, 607–614 (1954), i.e. in terms of the antiexudative action against the kaolin-induced edema in the hind paw of rats. The measurements were carried out by the method of Doepfner and Cerletti, Int. Arch. Allergy and Appl. Immunology 12, 89–97 (1958). The data thus obtained were plotted on a dose-activity graph, and from the resulting curve the dose which produces a 35% reduction in the edematons swelling ($ED_{35}$) was graphically calculated for each compound.

The acute toxicities of the compounds ($LD_{50}$) were determined in adult laboratory rats from the percentage of animals which died after administration of varying doses within an observation period of 14 days [see J. Pharmacol. exper. Therap. 96, 99 1949)].

The following table shows the result of these tests for a representative number of compounds according to the present invention, namely A = Cyclohexylamine salt of 4-(2'-nitro-4-biphenylyl)-4-hydroxy-butyric acid;

B = Cyclohexylamine salt of 4-(2'-amino-4-biphenylyl)-4-hydroxy-butyric acid;
C = Cyclohexylamine salt of 4-(2'-nitro-4-biphenylyl)-butyric acid;
D = Cyclohexylamine salt of 4-(2'-fluoro-4-biphenylyl)-butyric acid;
E = Cyclohexylamine salt of 4-(2'-chloro-4-biphenylyl)-4-hydroxy-butyric acid;
F = Cyclohexylamine salt of 4-(2'-chloro-4-biphenylyl)-butyric acid;
G = Cyclohexylamine salt of 4-(4'-nitro-4-biphenylyl)-butyric acid.

| Compound | $ED_{35}$ mgm/kg p.o. | $LD_{50}$ mgm/kg p.o. |
|---|---|---|
| A | 30 | > 500 (0 out of 5 animals died) |
| B | 66 | 1,340 |
| C | 66 | > 1,000 (3 out of 10 animals died) |
| D | 37 | > 500 (0 out of 10 animals died) |
| E | 27 | > 1,000 (1 out of 10 animals died) |
| F | 50 | > 1,000 (2 out of 10 animals died) |
| G | 30 | > 1,000 (0 out of 10 animals died) |

The analgesic activity of the compounds of the instant invention was ascertained by means of the writhing test.

For pharmaceutical purposes the compounds according to the present invention are administered to warm-blooded animals perorally or parenterally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like. One effective dosage unit of the compounds according to the present invention is from 0.83 to 6.7 mgm/kg, preferably 1.3 to 5.0 mgm/kg body weight, and the daily dose rate is 1.6 to 16.7 mgm/kg body weight.

The following examples illustrate a few pharmaceutical dosage unit compositions comprising a compound of the present invention as an active ingredient and represent the best modes contemplated of putting the invention into practical use. The parts are parts by weight unless otherwise specified.

EXAMPLE 64

Tablets

The tablet composition is compounded from the following ingredients:

| | |
|---|---|
| 4-(2'-Fluoro-4-biphenylyl)-butyric acid | 200.0 parts |
| Corn starch | 97.0 parts |
| Polyvinylpyrrolidone | 10.0 parts |
| Magnesium stearate | 3.0 parts |
| Total | 310.0 parts |

Preparation

The butyric acid compound is admixed with the corn starch, the mixture is granulated with an aqueous 14% solution of the polyvinylpyrrolidone through a 1.5 mm-mesh screen, the granulate is dried at 45° C and again passed through the screen, the dry granulate is admixed with the magnesium stearate, and the composition is compressed into 310 mgm-tablets with the aid of a conventional tablet making machine. Each tablet contains 200 mgm of the butyric acid compound and is an oral dosage unit composition with effective antiphlogistic action.

EXAMPLE 65

Coated pills

The pill core composition is compounded from the following ingredients:

| | |
|---|---|
| 4-(2'-Fluoro-4-biphenylyl)-4-hydroxy-butyric acid | 300.0 parts |
| Corn starch | 70.0 parts |
| Gelatin | 8.0 parts |
| Talcum | 18.0 parts |
| Magnesium stearate | 4.0 parts |
| Total | 400.0 parts |

Preparation

The butyric acid compound is admixed with the corn starch, the mixture is granulated with an aqueous 10% solution of the gelatin through a 1.5 mm-mesh screen, the granulate is dried at 45° C and again passed through the screen, the dry granulate is admixed with the talcum and the magnesium stearate, and the composition is compressed into 400 mgm-pill cores. These cores are subsequently coated in conventional manner with a thin shell consisting essentially of a mixture of talcum and sugar, and finally polished with beeswax. Each coated pill contains 300 mgm of the butyric acid compound and is an oral dosage unit composition with effective antiphlogistic action.

EXAMPLE 66

Gelatin capsules

The capsule filler composition is compounded from the following ingredients:

| | |
|---|---|
| 4-(2'-Fluoro-4-biphenylyl)-butyric acid | 200.0 parts |
| Corn starch | 190.0 parts |
| Colloidal silicic acid | 6.0 parts |
| Magnesium stearate | 4.0 parts |
| Total | 400.0 parts |

Preparation:

The ingredients are intimately admixed with each other, and 400 mgm-portions of the mixture are filled into No. 1 gelatin capsules. Each capsule contains 200 mgm of the butyric acid compound and is an oral dosage unit composition with effective antiphlogistic action.

EXAMPLE 67

Suppositories

The suppository composition is compounded from the following ingredients:

| | |
|---|---|
| 4-(2'-Fluoro-4-biphenylyl)-butyric acid | 300.0 parts |
| Suppository base (e.g. cocoa butter) | 1450.0 parts |
| Total | 1750.0 parts |

Preparation

The finely pulverized butyric acid compound is homogeneously blended with the aid of an immersion homogenizer into the suppository base which has previously been melted and cooled to 40° C. 1750 mgm-portions of the mixture are poured at 37° C into cooled suppository molds and allowed to harden therein. Each suppository contains 300 mgm of the butyric acid compound and is a rectal dosage unit composition with effective antiphlogistic action.

EXAMPLE 68

Hypodermic solution

The solution is compounded from the following ingredients:

| | |
|---|---|
| 4-hydroxy-4-(2'-Fluoro-4-biphenylyl)/butyric acid | 150.0 parts |
| IN Sodium hydroxide q.s.ad | pH 9.0 |
| Distilled water q.s.ad | 3000.0 parts by vol. |

Preparation

The butyric acid compound is suspended in a sufficient amount of distilled water and caused to go into solution by addition of the sodium hydroxide until pH 9. The solution is diluted to the indicated volume with additional distilled water, filtered until free from suspended particles, and the filtrate is filled into 3 ml-ampules which are sterilized for 20 minutes at 120° C and then sealed. Each ampule contains 150 mgm of the butyric acid compound, and the contents thereof are an injectable dosage unit composition with effective antiphlogistic action.

EXAMPLE 69

Suspension

The suspension is compounded from the following ingredients:

| | |
|---|---|
| 4-(2'-Fluoro-4-biphenylyl)-butyric acid | 4.0 parts |
| Dioctyl sodium sulfosuccinate (DONSS) | 0.02 parts |
| Benzoic acid | 0.1 parts |
| Sodium cyclamate | 0.2 parts |
| Colloidal silicic acid | 1.0 parts |

-continued

| | |
|---|---|
| Polyvinylpyrrolidone | 0.1 parts |
| Glycerin | 25.0 parts |
| Grapefruit flavoring | 0.1 parts |
| Distilled water q.s.ad | 100.0 parts by vol. |

Preparation

A sufficient amount of distilled water is heated to 70° C, and the DONSS, the benzoic acid, the sodium cyclamate and the polyvinylpyrrolidone are successively dissolved therein. The glycerin and the colloidal silicic acid are added to the solution, and the finely pulverized butyric acid compound is suspended in the mixture with the aid of an immersion homogenizer. Finally, the flavoring is added and the suspension is diluted to the indicated volume with distilled water. 5 ml of the suspension contain 200 mgm of the butyric acid compound and are an oral dosage unit composition with effective antiphlogistic action.

Analogous results are obtained when any one of the other compounds embraced by formulas I and Ia, or a non-toxic salt thereof, is substituted for the particular butyric acid compound in Examples 64 through 69. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. 4-(2'-fluoro-4-biphenylyl)-4-hydroxy-butyric acid or a non-toxic salt thereof formed with an inorganic or organic base.

* * * * *

UNITED STATES PATENT OFFICE
CERTIFICATE OF CORRECTION

Patent No. 4,021,479             Dated May 3, 1977

Inventor(s) ERNST SEEGER, WOLFHARD ENGEL, JOSEF NICKL and HELMUT TEUFEL

It is certified that error appears in the above-identified patent and that said Letters Patent are hereby corrected as shown below:

Col. 4, line 38 - "I2" should read -- Ia --

Col. 6, line 43 - "4'-4" should read -- 4'-(4 --

Col. 13, line 49 - "biphenyl" should read --biphenylyl --

Col. 13, line 55 - "biphenyl" should read -- biphenylyl --

Col. 14, line 61 - "biphenyl" should read -- biphenylyl --

Col. 15, line 15 "biphenyl" should read --biphenylyl --

Col. 16, line 16 - "2'4-biphenylyl" should read

-- 2'-amino-4-biphenylyl --

Signed and Sealed this

*sixteenth* Day of *August 1977*

[SEAL]

Attest:

RUTH C. MASON
*Attesting Officer*

C. MARSHALL DANN
*Commissioner of Patents and Trademarks*